(12) United States Patent
Viegas, Jr. et al.

(10) Patent No.: US 8,436,020 B2
(45) Date of Patent: May 7, 2013

(54) PROCESSES FOR THE PREPARATION OF PIPERIDINIC DERIVATIVES AND PHARMACEUTIC COMPOSITIONS CONTAINING THE SAME

(75) Inventors: Claudio Viegas, Jr., Quitandinha-Araraquara (BR); Vanderlan da Silva Bolzani, Quitandinha-Araraquara (BR); Eliezer Jesus de Lacerda Barreiro, Tijuca-Rio de Janeiro (BR); Newton G. Castro, Rio de Janeiro (BR); Maria Claudia Marx Young, Quitandinha-Araraquara (BR); Monica Santos Rocha, Leblon-Rio de Janeiro (BR)

(73) Assignees: Universidade Federal do Rio de Janeiro UBRJ, Rio de Janeiro (BR); Universidade Estadual Paulists UNESP, Quitandinha-Araraquara (BR)

( * ) Notice: Subject to any disclaimer, the term of this patent is extended or adjusted under 35 U.S.C. 154(b) by 0 days.

(21) Appl. No.: 13/517,548

(22) Filed: Jun. 13, 2012

(65) Prior Publication Data

US 2012/0323013 A1    Dec. 20, 2012

Related U.S. Application Data

(60) Division of application No. 13/104,251, filed on May 10, 2011, now abandoned, which is a division of application No. 11/734,949, filed on Apr. 13, 2007, now Pat. No. 8,258,303, and a division of application No. 11/576,864, filed on Apr. 6, 2007, now Pat. No. 8,273,893, said application No. 11/734,949 is a continuation-in-part of application No. 11/576,864, filed as application No. PCT/BR2004/000202 on Oct. 15, 2004.

(51) Int. Cl.
*A61K 31/445* (2006.01)
(52) U.S. Cl.
USPC .......................................... 514/326
(58) Field of Classification Search ................... 514/326
See application file for complete search history.

*Primary Examiner* — John Mabry
(74) *Attorney, Agent, or Firm* — Laurence P. Colton; Smth Risley Tempel Santos LLC

(57) ABSTRACT

Production processes for preparing pharmaceutical compositions containing new molecules capable of inhibiting acetylcholinesterase, thus being useful in the treatment of pathologies associated to cholinergic transmission, such as memory related disorders, neurodegenerative disorders such as Alzheimer's Disease, Miastenia Gravis or in the treatment of intoxications induced by chemical agents of central action.

4 Claims, 5 Drawing Sheets

PROCESSES FOR THE PREPARATION OF PIPERIDINIC DERIVATIVES AND PHARMACEUTIC COMPOSITIONS CONTAINING THE SAME

STATEMENT OF RELATED APPLICATIONS

This patent application is a divisional of U.S. patent application Ser. No. 13/104,251 having a filing date of 10 May 2011, currently pending. U.S. patent application Ser. No. 13/104,251 is a divisional of U.S. patent application Ser. No. 11/576,864 having a fling date of 6 Apr. 2007, currently pending, which is the Patent Cooperation Treaty (PCT) Chapter II National Phase of, and claims priority on, PCT International Patent Application No. PCT/BR2004/000202 having an International Filing Date of 15 Oct. 2004, both of which are incorporated herein by this reference. U.S. patent application Ser. No. 13/104,251 also is a divisional of U.S. patent application Ser. No. 11/734,949 having a filing date of 13 Apr. 2007, currently pending, which is a continuation-in-part of U.S. patent application Ser. No. 11/576,864 having a filing date of 6 Apr. 2007, which is the Patent Cooperation Treaty (PCT) Chapter II National Phase of, and claims priority on, PCT International Patent Application No. PCT/BR2004/000202 having an International Filing Date of 15 Oct. 2004. All of the above mentioned patent applications are incorporated herein by this reference.

BACKGROUND OF THE INVENTION

1. Technical Field

The present invention is concerned with pharmaceutical compositions containing new substances isolated from *Cassia spectabilis* (sin. *C. excelsa, Senna spectabilis*) as well as their semi-synthetic derivatives. In particular, the compositions derived from the present invention have demonstrated an acetylcholinesterase inhibitory profile, thus being useful in the treatment of memory related disorders and neurodegenerative diseases, such as Alzheimer's Disease and Parkinson's Disease. The present invention is also concerned with the processes of obtaining those compounds.

2. Related Art

Alzheimer's Disease (AD) is a neurodegenerative disease of great social-economic impact, being the cause of about 50-60% of the total number of dementia among people aged over 65 years old (Francis, P. T.; Palmer, A. M.; Snape, M.; Wilcock, G. K.; J. *Neurol Neurosurg Psychiatry* 1999, 66, 137). AD affects around 1.5% of the population with 65-69 years old, 21% with 85-86 years old and 39% with 90 years old or more, affecting approximately 15 million people in the world. This disease is considered one of the main health problems due to the tremendous impact to the patient, families, to the health system and to the society as a whole, since half of AD victims are inpatients at health institutions and the remaining half receive care treatment at home, involving families, relatives and friends. Quite often, AD patient care treatment brings tremendous emotional, psychological and financial stresses to the families involved, since treatment is expensive and the patient gradually loses their motor and cognitive functionalities, to the point of not recognizing close relatives. Scientists estimate that around 4 million people have AD and that AD incidence in the population over 65 years old duplicates every 5 years. Moreover, in the most industrialized countries, people over 65 years old are one of the most growing segments of the population, probably reaching at least 19 million people by the year 2050. Estimates say that half of this people will develop some form of AD.

The progressive degenerative process of psychomotor and cognitive functions, originally described by the German pathologist Alois Alzheimer in 1907, lasts about 8.5 to 10 years, from the appearance of the first symptoms until death occurs. The brain regions associated to high-level functions, particularly the neocortex and the hippocampus, are the most compromised by the biochemical alterations produced by AD (Francis, P. T.; Palmer, A. M.; Snape, M.; Wilcock, G. K.; *J. Neurol Neurosurg Psychiatry* 1999, 66, 137; Michaelis, M. L.; *J. Pharm. Exper. Ther.* 2003, 304, 897; Gooch, M. D.; Stennett, D. J.; *Am. J. Health Syst. Pharm.* 1996, 53, 1545). The occurrence of extracellular deposition of β-amyloid peptide (derivate from amyloid protein precursor—APP) in senile platelets and the erratic formation of intracellular neurofibriles (containing an abnormal phosphorilated form of a protein associated to microtubules—TAU) (Gooch, M. D.; Stennett, D. J.; *Am. J. Health Syst. Pharm.* 1996, 53, 1545; Francis, P. T.; Palmer, A. M.; Snape, M.; Wilcock, G. K.; *J. Neurol Neurosurg Psychiatry* 1999, 66, 137) are among the most evident causes of AD genesis. This process results in a loss of the neuronal function and synaptic damage, with subsequent compromising of memory, motor coordination and reasoning, added to loss of cognitive capacity and dementia.

At the cellular level, AD is associated to the reduction of acetylcholine (ACh) in the synaptic process, reducing the cortical cholinergic neurotransmission, apart from other neurotransmitters such as noradrenalin, dopamine, serotonin, glutamate and, in lower levels, substance P (Rufani, M.; Filocamo, L.; Lappa, S.; Maggi, A.; *Drugs in the Future* 1997, 22, 397; Tabarrini, O.; Cecchetti, V.; Temperini, A.; Filipponi, E.; Lamperti, M. G.; Fravolini, A.; *Bioorg. and Med. Chem.* 2001, 9, 2921). Recent studies demonstrated the reduction of the number of nicotinic and muscarinic ($M_2$) receptors for ACh, most of them present at pre-synaptic cholinergic terminations, with preservation of muscarinic ($M_1$ and $M_2$) post-synaptic receptors (Francis, P. T.; Palmer, A. M.; Snape, M.; Wilcock, G. K.; *J. Neurol Neurosurg Psychiatry* 1999, 66, 137).

The acetylcholine is biosynthesized from acetyl-coenzyme A (acetyl-coA) and choline by action of acetylcholinetransferase, which transfers an acetyl radical to choline, regenerating the Coenzyme-A. This neurotransmitter is found in the brain and in the neuromuscular junctions, composing part of the parasympathetic nervous system. The contraction of smooth muscles, blood vessels dilation and the control of heart beating are direct effects of ACh; in the brain, it is involved in the synaptic process and it is associated with motor control, memory and cognition. Its activity and permanence in the synaptic gap is regulated by acetylcholinesterase (AChE) catalyzed hydrolysis, which regenerates choline, its precursor. The active site of AChE responsible for the hydrolysis process is composed by a catalytic triad of serine (SER 200), hystidine (HIS 440) and glutamate (GLU 327). The AChE hydrolysis mechanism occurs by nucleophilic attack from serine to the carbonylic carbon of ACh, generating a tetraedric intermediate, stabilized by hydrogen bonds, producing free choline and acetylated serine. At the end, the hydrolysis of the serine acetyl group by water recovers the enzymatic site.

The basis of the cholinergic hypothesis is related to the capacity of drugs that, enhancing the central cholinergic function, could improve cognition and, perhaps, some of the behavioral effects induced by the disease. There are many alternatives to the correction of the cholinergic deficit, most of them focusing the substitution of ACh precursors (choline or lecithin). Nevertheless, these agents did not increase the central cholinergic activity (Francis, P. T.; Palmer, A. M.; Snape, M.; Wilcock, G. K.; *J. Neurol Neurosurg Psychiatry* 1999, 66, 137). Other studies investigated the use of cholinesterase inhibitors (ChE) for reducing ACh hydrolysis, e.g., phisostigmine. Recently, therapeutic approaches involving specific agonists of muscarinic receptors ($M_1$) and nicotinic or muscarinic antagonists ($M_2$) have been explored (Francis, P. T.; Palmer, A. M.; Snape, M.; Wilcock, G. K.; *J. Neurol Neurosurg Psychiatry* 1999, 66, 137; Gooch, M. D.; Stennett, D. J.; *Am. J. Health Syst. Pharm.* 1996, 53, 1545). Advances in the understanding of the evolution and molecular pathology of AD have shown that the use of AChE inhibitors should be the most efficient form of therapeutic approach to AD (Francis, P. T.; Palmer, A. M.; Snape, M.; Wilcock, G. K.; *J. Neurol Neurosurg Psychiatry* 1999, 66, 137; Rufani, M.; Filocamo, L.; Lappa, S.; Maggi, A.; *Drugs in the Future* 1997, 22, 397; Tabarrini, O.; Cecchetti, V.; Temperini, A.; Filipponi, E.; Lamperti, M. G.; Fravolini, A.; *Bioorg. and Med. Chem.* 2001, 9, 2921; Maelicke, A.; Schrattenholz, A.; Samochocki, M.; Radina, M.; Albuquerque, E. X.; *Behavioural Brain Res.* 2000, 113, 199; Quik, M.; Jeyarasasingam, G.; *Eur. J. Pharmacol.* 2000, 393, 223).

One of the therapeutic approaches to AD is the development of direct agonists of $M_1$ post-synaptic muscarinic receptors. As concrete examples of this research line, one could cite U.S. Pat. No. 4,211,867, U.S. Pat. No. 4,414,211 and U.S. Pat. No. 6,093,733, all of them describing new muscarinic agonist compounds. The stimulation of these receptors increased the cognition capacity in animals. However, despite the efforts in the development of $M_1$ agonists, many of the compounds tested have shown low selectivity, apart from various side effects due to the activation of $M_3$ receptors in the intestine, bladder and lung. $M_1$ non-selective agonists can also interact with $M_4$ and $M_5$ receptors in the central nervous system (CNS), with consequences not yet completely determined. Another possible cholinergic approach would be the development of antagonists to post-synaptic $M_2$ autoreceptors. Pharmacological data from animal models have demonstrated that the blocking of these receptors contributes to the increase of ACh levels and promotes better results in tests measuring the cognition capacity. Despite of the big number of potent $M_2$ antagonists published, very few show considerable selectivity when compared to other muscarinic receptors subtypes (Greenlee, W.; Clader, J.; Asberom, T. et al.; *II Farmaco* 2001, 56, 247).

The initial observation that muscarinic antagonists, such as scopolamine, produced deficits in short-term memory, lead to the idea that the cholinergic deficit was, predominantly, of muscarinic nature. However, this point of view changed due to a series of evidences, including autoradiographic and hystochemical studies from cerebral tissue autopsy, and also studies on brain images of patients, which demonstrated a more extensive specific loss of nicotinic receptors, in AD, in comparison to muscarinic receptors (Maelicke, A.; Schrattenholz, A.; Samochocki, M.; Radina, M.; Albuquerque, E. X.; *Behavioural Brain Res.* 2000, 113, 199; Maelicke, A.; Albuquerque, E. X.; *Eur. J. Pharmacol.* 2000, 393, 165; Maelicke, A.; Samochocki, M.; Jostock, R.; Fehrenbacher, A.; Ludwig, J.; Albuquerque, E. X.; Zerlin, M.; *Biol. Psych.* 2001, 49, 279).

Nowadays, there are many evidences showing that nicotinic drugs affect learning and memory. Nicotine and other nicotinic agonists can improve cognitive and psychomotor functions, while nicotinic antagonists cause cognitive deficit. Moreover, the occurrence of AD in smokers is smaller than in non-smokers, what may be associated to the overexpression of nicotinic receptor for ACh (nAChRs) observed in the brain of smokers. Thus, nicotinic drugs may exhibit chronic and acute effects in the cognitive function and, in addition, neuroprotection may be one of the chronic effects (Maelicke, A.; Albuquerque, E. X.; *Eur. J. Pharmacol.* 2000, 393, 165). Based on these findings, some scientists are looking for, with reasonable success, the creation of new nicotinic agonists, as in the case of WO 02/44176, WO 94/04152 and WO 03/022856.

Nicotinic receptors are expressed as various subtypes in mammals, being $\alpha 4\beta 2$ and $\alpha 7$ subtypes the most prominent and present in post-, pre-, peri-, and extra-synaptic locations. The nAChR $\alpha 7$ subtype receptors actions are very similar to subtype $\alpha 4\beta 2$, but presenting a much higher permeability to $Ca^{++}$, faster desensibilization and different pharmacology, including activation by Ch and blocking by $\alpha$-bungarotoxin (a snake toxin) (Maelicke, A.; Samochocki, M.; Jostock, R.; Fehrenbacher, A.; Ludwig, J.; Albuquerque, E. X.; Zerlin, M.; *Biol. Psych.* 2001, 49, 279). Due to choline sensitivity, nicotinic receptors $\alpha 7$ can be chemically excited even after the natural neurotransmitter being cleaved. Thus, this receptor subtype can respond not only to synaptic events, originated from the release of ACh, but also to volume alterations in the concentration of ACh/Ch. Moreover, due to its high permeability to $Ca^{++}$ ions, the activation of $\alpha 7$ receptors can produce metabotropic responses in excited cells, including the $Ca^{++}$ controlled release of transmitters and stimulation of genetic transcription and protein biosynthesis (Maelicke, A.; Samochocki, M.; Jostock, R.; Fehrenbacher, A.; Ludwig, J.; Albuquerque, E. X.; Zerlin, M.; *Biol. Psych.* 2001, 49, 279; Maelicke, A.; Albuquerque, E. X.; *Eur. J. Pharmacol.* 2000, 393, 165; Maelicke, A.; Schrattenholz, A.; Samochocki, M.; Radina, M.; Albuquerque, E. X.; *Behavioural Brain Res.* 2000, 113, 199).

Recently, three main strategies have been applied to balance nicotinic cholinergic deficits: stimulation of the ACh synthesis, inhibition of ACh degradation and administration of nicotinic receptors agonists. Actually, no therapeutic breakthrough has been obtained through the administration of ACh precursors; the administration of cholinesterase inhibitors, are the most common therapeutic alternative, producing the best results. Nevertheless, these inhibitors have limited therapeutic value and, in the great majority of the cases, are not capable in preventing the progression of AD at all (Maelicke, A.; Samochocki, M.; Jostock, R.; Fehrenbacher, A.; Ludwig, J.; Albuquerque, E. X.; Zerlin, M.; *Biol. Psych.* 2001, 49, 279; Maelicke, A.; Albuquerque, E. X.; *Eur. J. Pharmacol.* 2000, 393, 165; Maelicke, A.; Schrattenholz, A.; Samochocki, M.; Radina, M.; Albuquerque, E. X.; *Behavioural Brain Res.* 2000, 113, 199).

Many nicotinic receptors agonists are in clinical and preclinical trials, although of difficult dosage; higher levels may cause greater desensibilization than activation of nicotinic receptors. Other challenges, presently not solved, include the transport of the drug to the target brain nicotinic receptor (specific subtype of receptor) and the receptor subtype selectivity (Maelicke, A.; Albuquerque, E. X.; *Eur. J. Pharmacol.* 2000, 393, 165).

Given the latest breakthroughs in term of nicotinic receptors (physiology, biochemistry and genetic expression) and its effective participation in the events related to AD, the application of these receptors allosteric modulators has turned out to be a new strategy in the treatment of AD. Allosteric modulators are substances that interact with receptors through binding sites other than those used by ACh and by nicotinic antagonists and agonists. Since AD is associated to the reduction of nicotinic neurotransmission, allosteric modulators enhance the activity of nicotinic receptor channels in response to ACh. These properties gave birth to a new class of nAChR ligand, the allosteric potentiators ligands (APL) (Maelicke, A.; Samochocki, M.; Jostock, R.; Fehrenbacher, A.; Ludwig, J.; Albuquerque, E. X.; Zerlin, M.; *Biol. Psych.* 2001, 49, 279; Maelicke, A.; Albuquerque, E. X.; *Eur. J. Pharmacol.* 2000, 393, 165; Maelicke, A.; Schrattenholz, A.; Samochocki, M.; Radina, M.; Albuquerque, E. X.; *Behavioural Brain Res.* 2000, 113, 199).

The collinergic hypothesis is the most accepted biochemical theory and one of the most effective therapeutic strategies in the treatment of AD. Among the various mechanisms for increasing the cholinergic transmission, the inhibition of the acetylcholinesterase enzyme (AChE), a tetrametric protein responsible for the metabolic cleavage of ACh, is the most efficient method to improve the cholinergic deficit by increasing ACh levels in the central nervous system (CNS) and leading to a symptomatic improvement.

In spite of the fact that Miastenia Gravis (MG) is associated to a reduced number of cholinergic receptors in the neuromuscular junction, differently from Alzheimer Disease, where one finds neurotransmitter deficit, the hypothesis that the neurotransmitter metabolism phase via AChE inhibition could also alleviate MG symptoms exists. Thus, independently from a complete knowledge of the mechanisms involved, the availability of the new molecules, as the ones of the present invention, may be useful in the treatment of MG.

Among the available drugs in the market for the treatment of AD, tacrine (THA, Cognex®) was the first (synthetic) drug approved by the FDA (Food and Drug Administration) in the United States for therapeutical use, presenting a moderate effect, but meaningful in the relief of symptoms of moderate and low intensity forms of AD. However, its use is limited due to serious side effects, such as hepatotoxicity, forcing patients to interrupt the treatment (Rufani, M.; Filocamo, L.; Lappa, S.; Maggi, A.; *Drugs in the Future* 1997, 22, 397). Besides tacrine, at the present moment three other drugs are being commercialized in the USA and Europe for the treatment of AD: donepezil (Aricept®), rivastigmine (Exelon®) and galanthamine (Reminyl®). Among those, THA, donezepil and galanthamine are reversible AChE inhibitors, being galanthamine a natural product recently approved by FDA and serving as a prototype for the development of anticholinesterasic drugs (Rufani, M.; Filocamo, L.; Lappa, S.; Maggi, A.; *Drugs in the Future* 1997, 22, 397; Michaelis, M. L.; *J. Pharm. Exper. Ther.* 2003, 304, 897).

The structural diversity of known IAChEs and the possibility of exploring several mechanisms of action stimulated phitochemical studies over various vegetal species and over microorganisms, which may provide new models for anticholinesterasic substances. In this sense, various vegetal and microorganism species have been studied due to their popular use or ethno-botanic data. One of the most known examples of phytomedicine are *Ginkco* extracts. *Ginkco biloba* (Ginkgoaceae) is a tree that has been used for centuries in the traditional Chinese medicine for improving alertness. Today, *Ginkco* is probably the most used vegetal extract for improving cognitive function. Its use prevails specially in Europe, being recently approved in the treatment of dementia by the German Bundesgesundheit Association. Most of the evidences suggest that the enhancement of the cognitive function is associated to the use of a standard extract, the EGb 761. Measurement of the cognitive effects have been made on attention, learning, short-term memory, reaction time and choice time tests, but results appear to be not reproducible between different populations. Moreover, many studies have been published in journals of restricted circulation, what makes access to information harder; the majority of experiments in vivo, both in animals and humans, is restricted to a small number of individuals, compromising a conclusive and broad evaluation of the results (Gold, P. E.; Cahill, L.; Wenk, G. L.; *Psych. Sci. Publ. Int.* 2002, 3, 2).

Some studies using patients treated with a standard extract of *Ginkco biloba* and with placebo revealed effects compared to the ones obtained with donepezil, which is the drug of choice for the treatment of AD. Apparently, many of the protection effects over the CNS associated to the chronic use of *Ginkco* extract are related to the presence of terpenic components and flavonoids with antioxidant and anti-inflammatory properties. These substances can act in different forms, contributing to neuronal tissue integrity: (a) by inhibiting the activity of the superoxide dismutase and monoamino oxidase, which generate free radicals in the brain and in the body; (b) by capturing free radicals which may cause neuronal damage and consequently delay brain changes associated to the aging; (c) by reducing the release of arachdonic acid, a toxic co-product from lipid metabolism that appears in the brain just after an ischemic episode (Gold, P. E.; Cahill, L.; Wenk, G. L.; *Psych. Sci. Publ. Int.* 2002, 3, 2).

The necessity of turning research for phitochemical components, animals and microorganisms more objective and less expensive, lead to the development of numerous techniques of chemical and biochemical assays for monitoring and selection of biologically and pharmacologically useful extracts, extract fractions and pure substances. Regarding the search for AChE inhibitors, two bioautographical assays in thin layer chromatography have been recently developed (Hostettmann, K.; Queiroz, E. F.; Vieira, P. C.; *Principios Ativos de Plantas Superiores*, 1$^a$. ed., EdUFSCar: São Carlos, 2003). Marston and cols. (Marston, A.; Kissiling, J.; Hostettmann, K. A.; *Phytochem. Anal.* 2002, 13, 51) used an azoic colorant to identify the activity of AChE over 1-naftyl acetate; in another case Rhee and coleagues (Rhee, I. K.; van der Meent, M.; Ingkaninan, K.; Verpoorte, R.; *J. Chromatography A* 2001, 915, 217) used 5,5'-dithiobis(2-nitrobenzoic acid) (Ellmann's reagent) for the visualization of the enzymatic activity. Apparently, the only inconvenient in the use of Ellmann's reagent is the limit of visual detection, since in both cases white inhibition rings are formed over a blue colored plate (Marston and cols. assay) (Marston, A.; Kissiling, J.; Hostettmann, K. A.; *Phytochem. Anal.* 2002, 13, 51) and over a yellow colored plate (Rhee and cols. assay) (Hostettmann, K.; Queiroz, E. F.; Vieira, P. C.; *Principios Ativos de Plantas Superiores*, 1$^a$. ed., EdUFSCar: Sao Carlos, 2003).

A recent study with Brazilian plants (Trevisan, M. T. S.; Macedo, F. V. V.; van de Meent, M.; Rhee, I. K.; Verpoorte, R.; *Química Nova*, 2003, 26, 301) used the bioautographical assay of Rhee and cols. and Ellmann's assay in microplates to identify extracts which could contain AChE inhibitor substances (Rhee, I. K.; van der Meent, M.; Ingkaninan, K.; Verpoorte, R.; *J. Chromatography A* 2001, 915, 217; Ellmann, G. L.; *Biochem. Pharmacol.* 1961, 7, 88). Studies were made over 58 extracts of 30 species of various vegetal genuses, where authors considered an inhibition factor equal or greater than 50% as selection criteria for chemical fractionation. From the preliminary work, *Paullinia cupana* (guarana), *Amburana cearensis* (cumaru) and *Lippia sidoides* were the species that demonstrated the best results, inhibiting from 65 to 100% of the enzymatic activity in both bioassays. In the case of guarana, a positive effect on memory gain was observed after chronic and acute administration; up to now, 12 coumarins were isolated through the biodirected fractionation of extracts from *A. cearensis* and *L. sidoides*, demonstrating the usefulness of this type of assay for bioprospection of new anticholinesterasic drugs.

Galanthamine is an alkaloid isolated from various vegetal species of the Amaryllidaceae family and has revealed itself an AChE inhibitor of long, selective, reversible and competitive action, with therapeutic effects lasting even after the end of treatment (López, S.; Bastida, J.; Viladomat, F.; Codina, C.; *Life Sciences* 2002, 71, 2521). This is due to its double action mechanism: acting as an AChE inhibitor and on brain nicotinic receptors. The modulation of these receptors amplifies the neurotransmission of the AChE signal and characterizes a breakthrough in the design of drugs and AD treatments through nicotinic receptors allosteric modulator drugs (Rufani, M.; Filocamo, L.; Lappa, S.; Maggi, A.; *Drugs in the Future* 1997, 22, 397; Maelicke, A.; Schrattenholz, A.; Samochocki, M.; Radina, M.; Albuquerque, E. X.; *Behavioural Brain Res.* 2000, 113, 199; Quik, M.; Jeyarasasingam, G.; *Eur. J. Pharmacol.* 2000, 393, 223). The galanthamine acts by binding to the active site of cerebral AChE and also stimulates pre-synaptic and post-synaptic nicotinic receptors which can increase the release of neurotransmitters such as ACh and glutamate, directly stimulating the neuronal function (Fennel, C. W.; van Staden, J.; *J. Ethnopharm.* 2001, 78, 15). An excellent example among patents involving galanthamine analogs able to allosterically bind to receptors can be found in document WO 01/43697.

Another alkaloid isolated from *Narcissus* L. (Amaryllidaceae), the sanguinine (9-O-desmethylgalanthamine), proved to be 10 times more active than galanthamine itself in in vitro tests. The search for other AChE inhibiting substances (IAChE) in this vegetal genus, lead to the isolation of other two biologically active derivatives from galanthamine, the 11-hydroxigalanthamine and the epinorgalanthamine. Another structural type of alkaloid, licorine-like, has been isolated from this genus, being its most biologically active components the oxoassoanine, the assoanine and the pseudolicorine (López, S.; Bastida, J.; Viladomat, F.; Codina, C.; *Life Sciences* 2002, 71, 2521).

The study of various vegetal species currently used in Chinese popular medicine and in the Middle East lead to the isolation of various active alkaloids. An example of this is *Huperzia serrata* (syn.: *Lycopodium serratum*), used in a tea preparation prescribed for centuries in China for the treatment of fever and inflammation. The phytochemical study of this plant lead to the isolation of Huperzine A, an interesting candidate for the treatment of CNS disorders and epilepsy, capable of reducing neuronal loss caused by high concentrations of glutamate. It is a selective IAChE, very potent and its systemic use increases the release of ACh, dopamine and norepinephrine and the increase of ACh concentration lasts for up to 6 hours and has practically no action over the butyrylcholinesterase (BuChE) (Chang, J.; *Biochem. Pharmacol.* 2000, 59, 211; Rajendran, V.; Saxena, A.; Doctor, B. P.; Kozikowski, A. P.; *Bioorg. Med. Chem.* 2002, 10, 599). A new alkaloid *lycopodium*-like, the Huperzine P, was obtained from this same plant. However, its activity is lower than Huperzine A's.

Results obtained with Huperzine A encouraged Orhan and cols. to study other 5 *lycopodium* species in search for others AChE inhibitor metabolites (Orhan, I.; Terzioglu, S.; Sener, B.; *Planta Medica* 2003, 69, 265). After a preliminary evaluation of the extracts via Ellmann's ssay (Ellmann, G. L.; *Biochem. Pharmacol.* 1961, 7, 88), the extract of the aerial parts of the *L. clavatum* was selected and the bio-guided fractionation resulted in the isolation of the α-onocerin. The results from the anticholinesterasic activity demonstrated that the α-onocerine, which has an $IC_{50}$ equals to 5.2 μM, was better than donepezil in 1 to 3 mg/mL concentrations and practically equipotent in the 5 mg/mL concentration, though it did not reach the potency of galanthamine at any of the dosages tested. This performance called even more attention to huperzine, intensifying the search for structural analogs and resulting in many patent applications, such as WO 99/11625, WO 92/19238 and EP 806 416.

Some triterpenic alkaloids were isolated from *Buxus hyrcana*, such as homomoenjodaramine and moenjodaramine, and have proven promising AChE inhibitors (Ur-Rahman, A.; Choudhary, M. I.; *Pure Appl. Chem.* 1999, 71, 1079). From this family, *Buxus papillosa* provided other three steroidal alkaloids, selective AChE inhibitors: cycloprotobuxine C, cyclovirobuxeine A and cyclomicrophylline A (Ur-Rahman, A.; Parveen, S.; Khalid, A.; Farroq, A.; Choudhary, M. I.; *Phytochemistry* 2001, 58, 963).

Zeatine, initially described as an inductor agent of plantule growing, was isolated from *Fiatoua villosa*, which methanolic extract had been selected, after screening for inhibitory AChE activity. Pure zeatine inhibited AChE activity in a dosage-dependent mode with an $IC_{50}$ corresponding to $1.09 \times 10^{-4}$ M (Heo, H-J.; Hong, S-C.; Cho, H-Y.; Hong, B.; Kim, H-K.; Kim, E-K.; Shim, D-H.; *Mol. Cells* 2002, 13, 113).

The glycoalkaloids present in high concentrations at tomato skin (*Solanum tuberosum* L.) are responsible for many food poisoning cases. The observation of intoxicated patients revealed symptoms as mental confusion, depression and weakness. These effects were associated to the inhibition of AChE by α-solanine and α-chaconine, which correspond to 95% of glycoalkaloids present in *S. tuberosum* (Smith, D. B.; Roddick, J. G.; Jones, J. L.; *Trends in Food and Tech.* 1996, 7, 126).

Cultures of microorganisms, especially fungus of diverse families and genus, have been systematically studied as an important source in the search for useful drugs for the treatment of serious diseases such as cancer, malaria and bacterial infections, among many others. Otoguro, Kuno and colleagues (Kuno, F.; Otoguro, K.; Shiomi, K.; Iwai, Y.; Omura, S.; *J. Antibiot.* 1996, 49, 742; Kuno, F.; Shiomi, K.; Otoguro, K.; Sunazuka, T.; Omura, S.; *J. Antibiot.* 1996, 49, 748; Otoguro, K.; Kuno, F.; Omura, S.; *Pharmacol. Ther.* 1997, 76, 45), searching candidates for new drugs able to re-establish the neurotransmission system through the systematic screening of natural products produced by fungus, have discovered new AChE inhibitors, the arisugacines. From the soil fungus cultures WK-4164 and FO-4259, cyclophostin and arisugacines A and B were obtained, as well as the already known territrems B and C, and cyclopenine. Among those, arisugacine A, having an $IC_{50}$ of 1.0 nM, and arisugacine B, having an $IC_{50}$ of 25.8 nM, did not inhibit BuChE even in concentrations 20,000 times superior to 50% of inhibition of AChE activity, demonstrating a high selectivity and resulting in patented research and innovation as, for example, patent U.S. Pat. No. 6,384,045.

On the other hand, territrems B and C showed a lower selectivity, although their low $IC_{50}$, corresponding to 7.6 nM and 6.8 nM, respectively. The cyclopenine was the less active, with an $IC_{50}$ of 2,040 nM; however, it was quite selective, not inhibiting BuChE in concentrations up to 2,000 times higher to its $IC_{50}$. The cyclophostin, although very potent, with an $IC_{50}$ of 1.3 nM, was the less selective substance, inhibiting BuChE in dosages 35 times its $IC_{50}$ (Shiomi, K.; Tomoda, H.; Otoguro, K.; Omura, S.; *Pure Appl. Chem.* 1999, 71, 1059; Kuno, F.; Otoguro, K.; Shiomi, K.; Iwai, Y.; Omura, S.; *J. Antibiot.* 1996, 49, 742; Kuno, F.; Shiomi, K.; Otoguro, K.;

Sunazuka, T.; Omura, S.; J. Antibiot. 1996, 49, 748; Otoguro, K.; Kuno, F.; Omura, S.; Pharmacol. Ther., 1997, 76, 45).

Territrems A, B and C had already been isolated from *Aspergillus terreus* cultures and, despite the low selectivity demonstrated by the studies of Otoguro and cols. (Otoguro, K.; Kuno, F.; Omura, S.; *Pharmacol. Ther.* 1997, 76, 45), territrem B was approximately 20 times more potent than neostigmine in AChE inhibition. These results encouraged Peng (Peng, F-C.; *J. Nat. Prod.* 1995, 58, 857) to prepare territrem derivates for a structure-activity study. The evaluation of the enzymatic activity through Ellmann's assay did not reveal any potency increase for any of the semi-synthetic territrem derivates, though allowed the identification of the double bond in C-2, of the carbonyl in C-1, and of the intact pyrone unity as the essential pharmacophoric group for anticholinesterasic activity in this series of compounds.

The interest in AChE inhibitors from microorganisms metabolites, monitored by Ellmann's assay, lead Kim and cols. (Kim, W-G.; Song, N-K.; Yoo, I-D.; *J. Antibiot.* 2001, 54, 831) to investigate cultures of a new fungus, the *Penicillium citrinum* 90648. The diastereoisomers quinolactacins A1 and A2 were isolated from the solid fermentation of this microorganism. The anticholinesterasic activity evaluation of these substances revealed that isomer A2 presented an inhibitory AChE activity 14 times higher than the diastereoisomer A1. Its effect was dosage-dependent, showing an $IC_{50}$ of 19.8 µM, while isomer A1 has presented an $IC_{50}$ of only 280 µM. Moreover, the eutomer showed competitive inhibitory activity to the substratum and selective to AChE versus butyrylcholinesterase (BuChE), with an $IC_{50}$ of 650 µM, by using tacrine as positive control in all tests ($IC_{50\ BuChE}$=0.006 µM, $IC_{50\ AChE}$=0.12 µM, very low selectivity).

*Cassia spectabilis*, a very well known leguminosae from middle-west Brazil, has been extensively studied by our research group, seeking for piperidine alkaloids presenting bio- and pharmacological activity. The phytochemical study of leaves, fruits and flowers from this leguminosae provided around 12 2,6-alkyl-piperidin-3-ols and derivates that showed weak selective cytotoxicity in mutant lineage of *Saccharomyces cerevisiae*. The poorly significant cytotoxic activity of these alkaloids induced us to explore other pharmacologic assays which could confirm some ethnopharmacologic data of the *Cassia* genus. Thus, assays for central and peripheral analgesic activity, anti-inflammatory activity and AChE inhibitory activity were performed (Bolzani, V. S.; Gunatilaka, A. A. L.; Kingston, D. G. I., "Bioactive and other piperidine alkaloids from *Cassia leptophylla*", *Tetrahedron* 1995, 51(21), 5929-5934; Moreira, M. S. A.; Viegas Jr., C.; Miranda, A. L. P. Bolzani, V. S.; Barreiro, E. J., "Analgesic profile of (−)-spectaline: a piperidine alkaloid from *Cassia leptophylla* Vog. (Leguminosae)", *Planta Medica* 2003, submitted; Viegas Jr., C., PhD thesis, UNESP-Araraquara/SP, 2003, unpublished data; Viegas Jr., C.; Young, M. C. M.; Bolzani, V. S.; Rezende, A.; Barreiro, E. J., "Estudo Fitoquimico de *Cassia leptophylla* biomonitorado por linhagens transgenicas de *S. cerevisiae*", 24$^a$ Reunião Anual da Sociedade Brasileira de Química, Poços de Caldas-MG, 2001, PN-075; Barreiro, E. J.; Bolzani, V. S.; Viegas Jr. C., "Novos Alcalóides Piperidínicos Isolados das Flores de *Cassia leptophylla* (Leguminosae), 25$^a$ Reunião Anual da Sociedade Brasileira de Química, Poços de Caldas-MG, 2002, PN-058). The biggest amounts of (−)-3-O-acetylspectaline and of (−)-spectaline came from the flowers of this plant, which were submitted to several chemical modifications in order to obtain new derivatives. The chloridrate derivatives LASSBio-767, LASSBio-768 and LASSBio-822 were evaluated in respect to AChE inhibitory capacity ex vivo and demonstrated remarkable anticholinesterasic activity. In spite of the novelty about the molecular structure of these new derivatives, many other piperazinic compounds (the compounds of interest are piperidinic alkaloids) presenting anticholinesterasic activity had already been described, being part of the state of the art. Examples of this intellectual production may be found in documents WO 00/33788, which describes nitrogenated heterocyclics capable of act in neurological disorders and not revealing its mechanism of action, although stating that the compounds are weak inhibitors of AChE, and WO 92/17475, EP 1 300 395 and EP 1 116 716, which describe anticholinesterasic piperidinic and piperazinic derivates, diverse from the compounds introduced here. However, there is no report on the use of the molecules targeted by the present invention as anticholinesterasic substances or for the treatment of memory disorders, neurodegenerative disorders, or intoxications by central action substances.

BRIEF SUMMARY OF THE INVENTION

It is an object of the present invention to provide pharmaceutical compositions for AChE inhibition. In one aspect of this invention, these pharmaceutical compositions are obtained from piperidine alkaloids from *C. spectabilis* and their semi-synthetic derivatives, specially the compounds 2-(R)-methyl-3-(R)-O-acetyl-6-(S)-(tetradecyl-13'-one)-piperidine, 2-(R)-methyl-6-(S)-(tetradecyl-13'-one)piperidin-3-(R)-ol and 2-(R)-methyl-3-(R)—O-ter-butoxycarbonyl-6-(S)-(tetradecyl-13'-one)-piperidine and their respective cloridrates.

The pharmaceutical compositions of the present invention, due to its ability of inhibiting AChE, can be used in the treatment of pathologies associated to cholinergic transmission such as neurodegenerative diseases, e.g. Alzheimer's Disease and Parkinson's Disease, and other pathologies associated to memory deficiency conditions.

In another aspect, the pharmaceutical compositions of the present invention, also due to its ability of inhibiting AChE, can be used in the treatment of other conditions associated to cholinergic transmission, for example, muscular diseases such as Miastenia Gravis and muscular paralysis conditions resulting from the military use of biological and/or chemical agents.

An additional object of this invention is to provide processes for obtaining the pharmaceutical compositions of the present invention

DETAILED DESCRIPTION OF PREFERRED EMBODIMENTS

Figure 1:
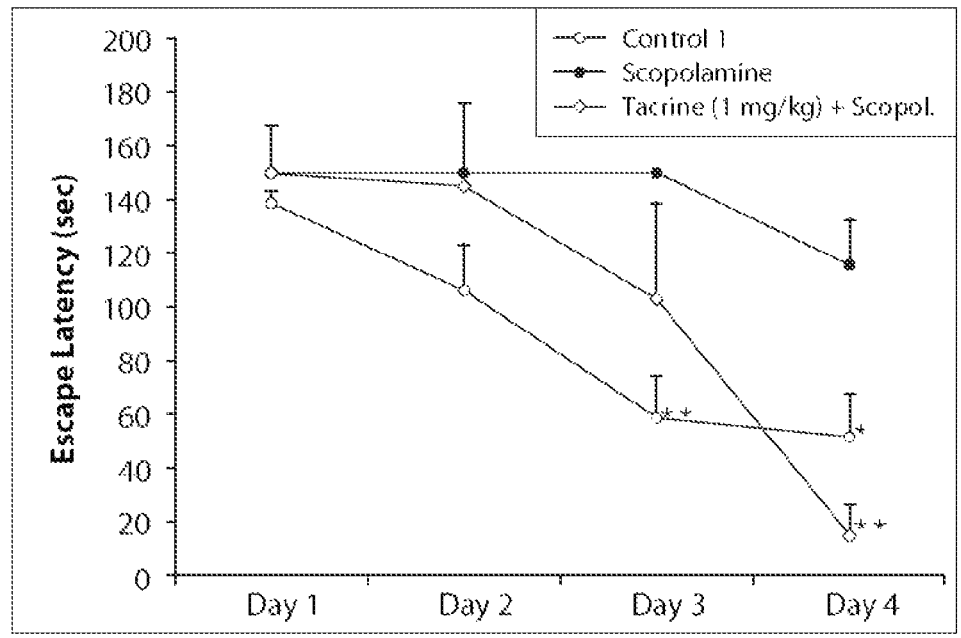
FIG. 1 shows the effect of tacrine (1 mg/kg) in the reversion of amnesia induced by scopolamine in the water maze test. The histogram shows the escape latency (in seconds) during the 4 days test of the control group (-µ-), scopolamine (-λ-) and tacrine+scopolamine (-◇-). Values expressed as average and standard deviation; *p<0.05; **p<0.01 Mann-Whitney test.
Figure 2:
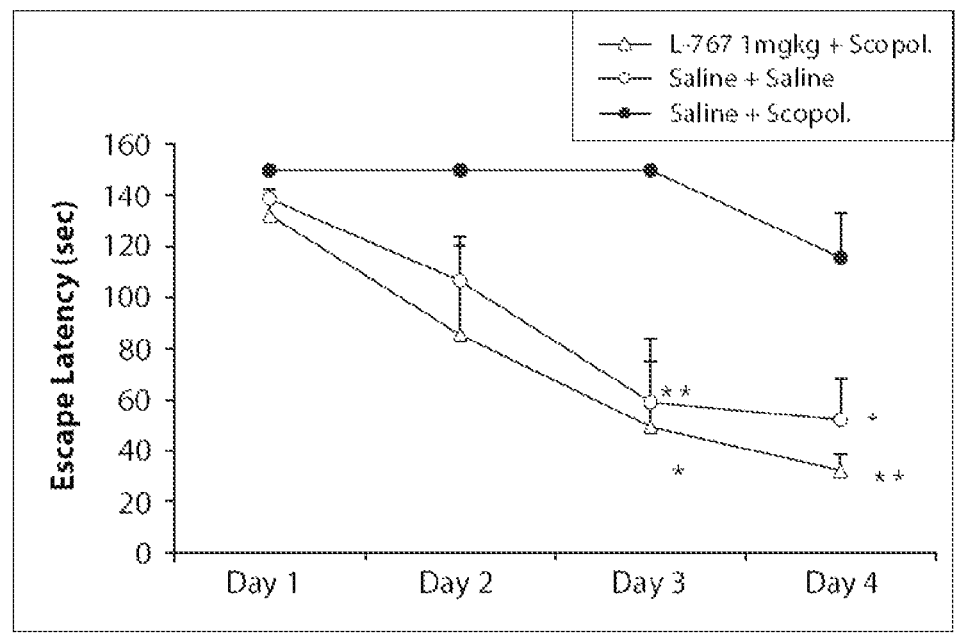
FIG. 2 presents the effect of the semi-synthetic alkaloid LASSBio-767, in the 1 mg/kg concentration, in the reversion of amnesia induced by scopolamine in the water maze test. The histogram shows the escape latency (in seconds) during the 4 days test of the control group (-µ-), scopolamine (-λ-) and LASSBio-767+scopolamine (-◇-). Values expressed as average and average standard deviation; *p<0.05; **p<0.01 Mann-Whitney test.
Figure 3:
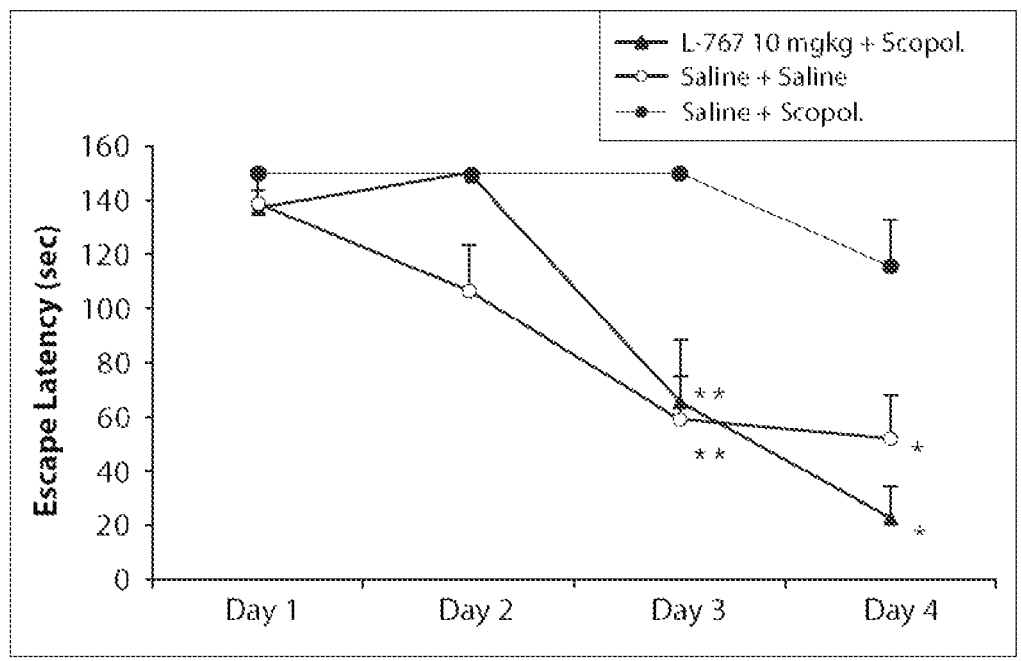
FIG. 3 presents the effect of the semi-synthetic alkaloid LASSBio-767, in the 10 mg/kg concentration, in the reversion of amnesia induced by scopolamine in the water maze test. The histogram shows the escape latency (in seconds) during the 4 days test of the control group (-μ-), scopolamine (-λ-) and LASSBio-767+scopolamine (-◇-). Values expressed as average and average standard deviation; $*p<0.05$; $**p<0.01$ Mann-Whitney test.
Figure 4:
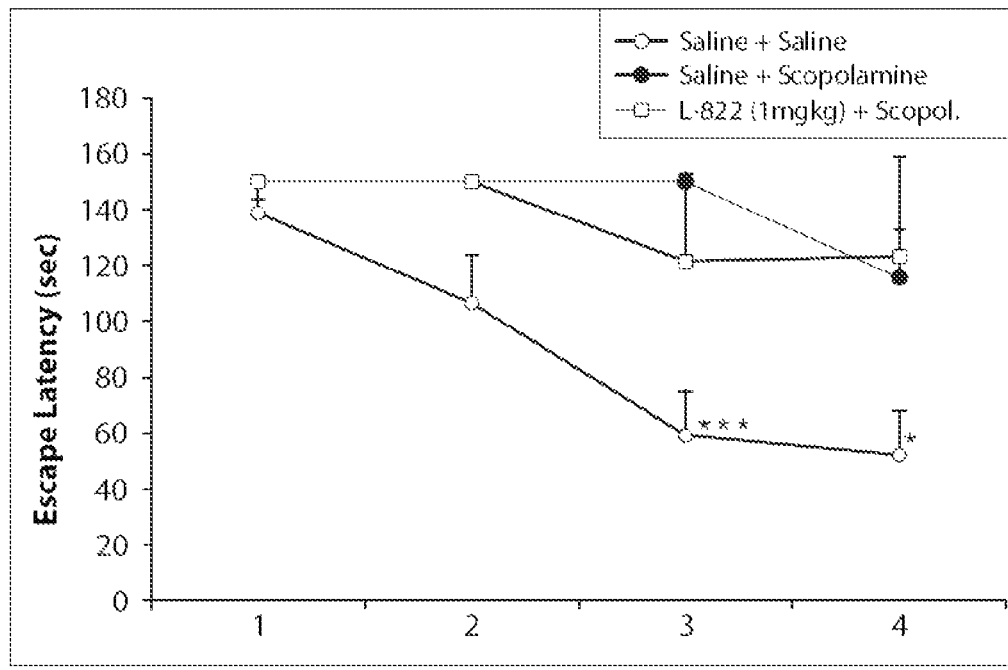
FIG. 4 presents the effect of the semi-synthetic alkaloid LASSBio-822, in the 1 mg/kg concentration, in the reversion of amnesia induced by scopolamine in the water maze test. The histogram shows the escape latency (in seconds) during the 4 days test of the control group (-μ-), scopolamine (-λ-) and LASSBio-822+scopolamine (-◇-). Values expressed as average and average standard deviation; $*p<0.05$; $**p<0.01$ Mann-Whitney test.

For the purposes of this invention, "pharmaceutical compositions" is understood as any composition containing an active principle, with prophylactic, palliative and/or curative properties, acting towards maintaining and/or restoring homeostasis, being administered via topic, parenteral, enteral and/or, intrathecal forms. Also for the purposes of this invention, "active principle" is understood by all or any substance expressed by formulas (I) or (II), or its acceptable pharmaceutical salts.

The new substances object of this invention belong to the class of piperidine alkaloids, of general structure (I):

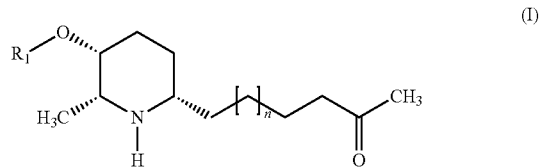

(I)

wherein:

n corresponds to an integer number from 2 to 16

$R_1$ is hydrogen, acyl, alkyl, alkoxyl, cycloalkyl; furyl, tiophenyl, pyridinyl, pyrimidinyl, pyrrolyl, thiazolyl, quinazolyl, isoquinolyl or Phenyl-W;

wherein W is hydrogen, ortho-alkyl, ortho-cycloalkyl, ortho-alkoxyl, ortho-cycloalkoxyl, ortho-thioxy, ortho-aryloxy, ortho-sulfones, ortho-sulfides, ortho-sulfoxides, ortho-sulfonates, ortho-sulfonamides, ortho-amino, ortho-amido, ortho-halo, ortho-carboalkoxy, ortho-carbothioalkoxy, ortho-trihaloalkane, ortho-cyano, ortho-nitro, meta-alkyl, meta-cycloalkyl, meta-alkoxyl, meta-cycloalkoxyl, meta-thioxy, meta-aryloxy, meta-sulfones, meta-sulfides, meta-sulfoxides, meta-sulfonates, meta-sulfonamides, meta-amino, meta-amido, meta-halo, meta-carboalkoxy, meta-carbothioalkoxy, meta-trihaloalkane, meta-cyano, meta-nitro, para-alkyl, para-cycloalkyl, para-alkoxyl, para-cycloalkoxyl, para-thioxy, para-aryloxy, para-sulfones, para-sulfides, para-sulfoxides, para-sulfonates, para-sulfonamides, para-amino, para-amido, para-halo, para-carboalkoxy, para-carbothioalkoxy, para-trihaloalkane, para-cyano or para-nitro.

The new substances also object of this invention belong to the class of derivatives of general structure (I), of general structure (II):

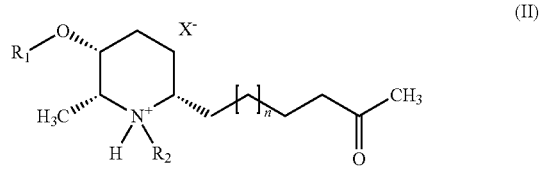

(II)

wherein:

n corresponds to an integer number from 2 to 16

$R_1$ is hydrogen, acyl, alkyl, alkoxyl, cycloalkyl; furyl, tiophenyl, pyridinyl, pyrimidinyl, pyrrolyl, thiazolyl, quinazolyl, isoquinolyl or Phenyl-W;

wherein W is hydrogen, ortho-alkyl, ortho-cycloalkyl, ortho-alkoxyl, ortho-cycloalkoxyl, ortho-thioxy, ortho-aryloxy, ortho-sulfones, ortho-sulfides, ortho-sulfoxides, ortho-sulfonates, ortho-sulfonamides, ortho-amino, ortho-amido, ortho-halo, ortho-carboalkoxy, ortho-carbothioalkoxy, ortho-trihaloalkane, ortho-cyano, ortho-nitro, meta-alkyl, meta-cycloalkyl, meta-alkoxyl, meta-cycloalkoxyl, meta-thioxy, meta-aryloxy, meta-sulfones, meta-sulfides, meta-sulfoxides, meta-sulfonates, meta-sulfonamides, meta-amino, meta-amido, meta-halo, meta-carboalkoxy, meta-carbothioalkoxy, meta-trihaloalkane, meta-cyano, meta-nitro, para-alkyl, para-cycloalkyl, para-alkoxyl, para-cycloalkoxyl, para-thioxy, para-aryloxy, para-sulfones, para-sulfides, para-sulfoxides, para-sulfonates, para-sulfonamides, para-amino, para-amido, para-halo, para-carboalkoxy, para-carbothioalkoxy, para-trihaloalkane, para-cyano or para-nitro.

$R_2$ is either hydrogen or alkyl with 1 to 9 carbon atoms, and X is halogen;

The new substances also object of this invention belong to the class of derivatives of general structure (I), of general structure (III):

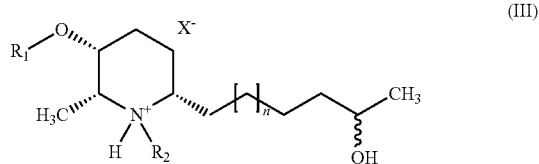

wherein:

n corresponds to an integer number from 2 to 16

$R_1$ is hydrogen, acyl, alkyl, alkoxyl, cycloalkyl; furyl, tiophenyl, pyridinyl, pyrimidinyl, pyrrolyl, thiazolyl, quinazolyl, isoquinolyl or Phenyl-W;

wherein W is hydrogen, ortho-alkyl, ortho-cycloalkyl, ortho-alkoxyl, ortho-cycloalkoxyl, ortho-thioxy, ortho-aryloxy, ortho-sulfones, ortho-sulfides, ortho-sulfoxides, ortho-sulfonates, ortho-sulfonamides, ortho-amino, ortho-amido, ortho-halo, ortho-carboalkoxy, ortho-carbothioalkoxy, ortho-trihaloalkane, ortho-cyano, ortho-nitro, meta-alkyl, meta-cycloalkyl, meta-alkoxyl, meta-cycloalkoxyl, meta-thioxy, meta-aryloxy, meta-sulfones, meta-sulfides, meta-sulfoxides, meta-sulfonates, meta-sulfonamides, meta-amino, meta-amido, meta-halo, meta-carboalkoxy, meta-carbothioalkoxy, meta-trihaloalkane, meta-cyano, meta-nitro, para-alkyl, para-cycloalkyl, para-alkoxyl, para-cycloalkoxyl, para-thioxy, para-aryloxy, para-sulfones, para-sulfides, para-sulfoxides, para-sulfonates, para-sulfonamides, para-amino, para-amido, para-halo, para-carboalkoxy, para-carbothioalkoxy, para-trihaloalkane, para-cyano or para-nitro.

$R_2$ is either hydrogen or alkyl with 1 to 9 carbon atoms, and X is halogen;

For the sake of clearness, the following terminology will be adopted for chloridrate derivatives: LASSBio-767 corresponds to the derivative of general formula (II) where $R_1$ corresponds to acetyl, $R_2$ is hydrogen, X is chloride and n is equal to 9; LASSBio-768 corresponds to the derivative of general formula (II) where $R_1$ corresponds to H, $R_2$ is hydrogen, X is chloride and n is equal to 9; LASSBio-822 corresponds to the derivative of general formula (II) where $R_1$ corresponds to t-butoxycarbonyl, $R_2$ is hydrogen, X is chloride and n is equal to 9; LASSBio-795 corresponds to the derivative of general formula (II) where $R_1$ corresponds to acetyl, $R_2$ is methyl, X is iodine and n is equal to 9; and LASSBio-783 corresponds to the derivative of general formula (III) where $R_1$ corresponds to acetyl, $R_2$ is hydrogen, X is chloride and n is equal to 9.

The following examples are for illustrative purpose only, not limiting the different ways of performing the invention.

EXAMPLE 1

Production and Structural Identification of the Natural Substrates Corresponding to General Formula (I)

The ethanolic extract of flowers and buds from *C. spectabilis* was concentrated, yielding 39.7 g of crude material, which was dissolved in a methanol-water 8:2 mixture. The mixture was submitted to ultra-sound and the insoluble residue, weighting 10.4 g, was removed via paper filtering. The hydroalcoholic solution was submitted to a liquid-liquid extraction, from which the following subfractions were obtained: hexane (2.0 g), dichloromethane (7.96 g), ethyl acetate (0.34 g), n-butanol (2.5 g) and aqueous (11.9 g).

A portion of the dichloromethane subfraction, weighting 3.25 g, was dissolved in 100 mL of chloroform, followed by successive extractions of 50 mL portions of 40% aqueous HCl, under magnetic stirring for 15 minutes each, making a total of 4 portions. The aqueous extracts were combined and alkalinized with concentrated aqueous solution of $NH_4OH$ up to pH 9-11, followed by successive extractions with chloroform (3×50 mL) and ethyl acetate (3×50 mL). The chloroform and ethyl acetate extracts were combined yielding 1.45 g of an alkaloidic mixture. This mixture was fractionated in chromatographic column with 44 g of neutral alumina as stationary phase. The alkaloidic mixture (1.45 g) was added followed by elution with a chloroform/hexane (9:1 to 9.5:0.5) mixture and by chloroform/methanol/hexane (8:0.5:1.5 up to 9:1:0) mixture, resulting in the production of 910 mg of a compound corresponding to general formula (I) when R is H (espectaline), and 151 mg of a compound corresponding to general formula (I) when R is acetyl (3-O-acetyl-ethyl espectaline).

The yield of this chromatographic procedure of espectaline was 28% from the dichloromethane subfraction, and 5% from the flowers and buds crude extract from of *C. spectabilis*, while the 3-O-acetyl-espectaline was obtained from the dichloromethane subfraction with 4.6% yield.

The compounds spectaline and 3-O-acetyl-espctaline had their chemical structures confirmed by polarimetric data, melting point and NMR spectrometric data of uni- and bi-dimensional $^1H$ and $^{13}C$, infrared (IR) and mass spectrometry (MS). The espctaline was identified by comparison with laboratory available data, as being (−)-espectaline, and the 3-O-acetyl-espectaline was characterized as a natural derivative from espectaline, the (−)-3-O-acetyl-espectaline.

EXAMPLE 2

Production of Semi-Synthetic Derivates, Chlorhydrates, Corresponding to General Formula (II)

a) Synthetic approach to the preparation of 2-(R)-methyl-3-(R)—O-t-butoxycarbonyl-6-(S)-(tetradecyl-13'-one)-piperidine To a solution of espectaline (0.5 g; 1.54 mmol) under $N_2$ atmosphere and in 15 mL of dry $CH_2Cl_2$, dry $Et_3N$ was added 0.3 mL (2.156 mmol), resting 5 min under stirring at room temperature. Afterwards, a solution of $(Boc)_2O$ (369 mg; 1.694 mmol) in 15 mL $CH_2Cl_2$ was added and rested under stirring at room temperature for 24 h, being monitored by TLC. Then a catalytic amount of 4-DMAP and more 100 mg $(Boc)_2O$ were added, keeping the stirring under $N_2$ atmosphere for 4 more days.

After complete conversion of the starting material, 10 mL of water was added, followed by extraction with $CHCl_3$ (4×10 mL). The organic phases were then combined and washed with aq. HCl 2N (3×10 mL) followed by brine (2×10 mL). The organic phase was then dried with $MgSO_4$, filtered and concentrated under reduced pressure.

The raw product was purified in neutral $Al_2O_3$ column with $CHCl_3$/Hex/MeOH as eluent to give 280.5 mg of the desired carbonate 3-O-Boc-espectaline together with the corresponding carbamate byproduct, in a 60% yield.

The reaction product was characterized by $^1H$ and $^{13}C$ NMR. The melting point of 3-O-Boc-espectaline derivative was 57.5-60° C.

b) Preparation of 2-(R)-methyl-3-(R)—O-acetyl-6-(S)-(tetradecyl-13'-one)-piperidine chlorhydrate (LASSBio-767)

In a single neck flask, 15 mg of 2-(R)-methyl-3-(R)—O-acetyl-6-(R)-(tetradecyl-13'-one)-piperidine (0.041 mmol) was dissolved in 3 mL of dry dichloromethane was dissolved. In a Keeper system conc. HCl was added and then conc. $H_2SO_4$ was slowly added, letting the HCl (g) pass through the reaction system. The reaction was kept for 45 min., always adding dichloromethane to maintain the starting solvent level. At the end, the solvent evaporated, and a solid material was formed in the flask walls. This material was redissolved in dichlormethane and concentrated in a rotatory evaporator. LASSBio-767 was obtained in quantitative amounts and was characterized by $^1H$ and $^{13}C$ NMR, and through physical-chemical data. The water-soluble derivative presented melting point of 142.8-147.5° C.

The same experimental procedure was used for the preparation of espectaline chlorhydrate, which was obtained in quantitative amounts from the natural substrate, (−)-espectaline. Its characterization was made by $^1H$ and $^{13}C$ NMR and through physical-chemical data. The water-soluble derivative presented melting point of 149.1-151.1° C.

c) Synthetic Approach to the Production of Espectaline Chlorhydrate from 2-(R)-methyl-6-(S)-(tetradecyl-13'-one)-piperidin-3-(R)-ol (LASSBio-768)

In a single neck flask coupled with a reflux condenser, 375 mg (1.15 mmol) of 2-(R)-methyl-6-(S)-(tetradecyl-13'-one)-piperidin-3-(R)-ol was dissolved in 10 mL of ethyl acetate, followed by the addition of 4 mL fuming HCl. The reaction system was kept at room temperature for 10 h and under reflux for 4 h. At the end, the solvent was evaporated, the product was redissolved in methanol, dried with anhydrous $MgSO_4$, filtered and solvent evaporated. After drying under vacuum, the compound LASSBio-768 was quantitatively obtained.

In a double neck flask coupled with a reflux condenser and under $N_2$ atmosphere, the compound LASSBio-767 (114 mg, 0.31 mmol) was dissolved in 5 mL of anhydrous chloroform. With the aid of a syringe, fresh distilled acetyl chloride (0.1 mL, 1.42 mmol) was added and let react during 12 h at 50° C. At the end, the solvent was evaporated and the remaining was dried under vacuum to obtain the compound LASSBio-767 with 93% yield.

d) Synthetic Approach to the Production of 2-(R)-methyl-3-(R)—O-ter-butoxycarbonyl-6-(S)-(tetradecyl-13'-one)-piperidine chlorhydrate (LASSBio-822)

The same experimental procedure described for the LASSBio-767 chlorhydrate production was used in the preparation of LASSBio-822 chlorhydrate from 3-O-Boc-espectaline. The derivative LASSBio-822 was obtained in quantitative amount and was characterized through $^1H$ and $^{13}C$ NMR. The water-soluble derivative LASSBio-822 presented melting point of 126-129.5° C.

e) Synthetic Approach to the Production of (2R,3R,6S)-3-acetoxy-6-(13-hydroxy-tetradecyl-2-methyl)-piperidine chlorhydrate (LASSBio-783)

The experimental procedure for the preparation of this derivative is based on a simple carbonyl reduction, through a number of reactions known by any technician in the area as, for example, the reaction of $NaBH_4$ in $H_2O$ at room temperature.

EXAMPLE 3

Pharmacological Evaluation a) Anticholinesterasic Activity Assay

The anticholinesterasic effect of the compounds from the present invention is herein demonstrated, among other effects, by the results of the compounds LASSBio-767, LASSBio-768 and LASSBio-822. The compounds from the present invention were investigated in the brain tissue of rat, where the main form of the expressed enzyme, like in humans, is the tetramer of T type sub-unities, which are linked to membranes through hydrophobic chains (Boschetti, N.; Liao, J.; Brodbeck, U. The Membrane Form of Acetylcholinesterase From Rat Brain Contains a 20 KDa Hydrophobic Anchor. *Neurochem. Res.* 1994, 19, 359-365; Fernandez, H. L.; Moreno, R. D.; Inestrosa, N. C. Tetrameric (G4) Acetylcholinesterase: Structure, Localization, and Physiological Regulation. *J. Neurochem.* 1996, 66, 1335-1346). Ellman's colorimetric assay (Ellman, G. L.; Courtney, K. D.; Andres, V.; Featherstone, J.; Featherstone, R. M. A New and Rapid Colorimetric Determination of Acetylcholinesterase Activity. *Biochem. Pharmacol.* 1961, 7, 88-95) was adapted for determination of the total activity of cholinesterase in homogenized rat brain. Brain tissue of Wistar rats were homogenized in 2% v/v buffer sodium phosphate 0.1M, pH 7.4, with the addition of NaCl 58.5 g/L and Triton X-100 0.05% v/v. Fractions of the homogenized mixture (204) were incubated with the anticholinesterasic compounds for 10 minutes in pH 8 phosphate buffer before the addition of 5,5'-dithiobis(2-nitrobenzoic) acid and also of 1 mM of acetylthiocholine iodide (SIGMA, USA). The reaction was conducted at room temperature (22-25° C.), in 235 µL at microplates with 96 wells, followed by microplate reader (SpectraMAX 250, Molecular Devices, USA) at 412 nm during 5 minutes. In all experiments, cholinesterase-independent substrate hydrolysis (non specific) was determined by the inclusion of an experimental group treated with THA 20 µM. Appropriate tissues and reagents (em branco) were also included. Reaction velocities were determined in 3 or 4 repetitions by condition; mean values were calculated and expressed as percentages of relative activity in respect to control (solvent), after subtraction of the non-specific hydrolysis rate. The substances were tested in at least five different concentrations. From the resulting inhibition curve, values in the ranges outside 20%-80% were considered, with concentration limited to 500 µM. The $IC_{50}$, based in a single-site model, was determined via linear regression. Results were expressed as Mean±SEM of the $IC_{50}$, obtained independently from 2 to 4 animals, and are presented in Table 1 below.

TABLE 1

| Compound | Experimental IC$_{50}$ | | | | N | Mean | SD* | SEM** |
|---|---|---|---|---|---|---|---|---|
| | | | Cerebral cholinesterase inhibition data. | | | | | |
| Tacrine | THA (09/08/00) 0.173433 | THA (10/08/00) 0.224864 | THA (11/07/01) A 0.110992 | THA (11/07/01) B 0.112401 | 4 | 0.16 | 0.05 | 0.03 |
| Galanthamine | Gal (11/07/01)A 3.284665 | Gal (11/07/01) B 2.923275 | | | 2 | 3.10 | 0.26 | 0.18 |
| LASSBio 767 | 767 (22/11/01-r2) 4.817214 | 767 (29/11/01) 4.486283 | | | 2 | 4.65 | 0.23 | 0.17 |
| LASSBio 768 | 768 (22/11/01) 194.541473 | 768 (29/11/01) 278.128845 | | | 2 | 236.34 | 59.11 | 41.79 |
| LASSBio 783 | 783 (28/3/03-rA) 333.033844 | 783 (4/4/03-rB) 701.750244 | 783 (4/4/03-rC) 241.899277 | | 3 | 425.56 | 243.49 | 140.58 |
| LASSBio 795 | 795 (26/3/03-rA) 173.047897 | 795 (1/4/03-rB) 232.144257 | 795 (1/4/03-rC) 325.254974 | | 3 | 243.48 | 76.73 | 44.30 |
| LASSBio 822 | 822 (28/3/03-rA) 9.154104 | 822 (8/4/03-rB) 16.217253 | 822 (8/4/03-rC) 19.869019 | | 3 | 15.08 | 5.45 | 3.14 |

*Standard Deviation.
**Standard Error of the Mean.

b) Evaluation of the Induced Amnesia by Scopolamine in the Morris Water Maze

A total of 39 Wistar rats (females—±200 g) were used. Animals were divided into 5 experimental groups and respective control groups:

control=saline+saline–11 animals saline+scopolamine (1 mg/kg)–8 animals tacrine (1 mg/kg)+scopolamine (1 mg/kg)–4 animals LASSBio-767 (1 mg/kg)+scopolamine (1 mg/kg)–4 animals LASSBio-767 (3 mg/kg)+scopolamine (1 mg/kg)–4 animals LASSBio-767 (10 mg/kg)+scopolamine (1 mg/kg)–4 animals LASSBio-822 (1 mg/kg)+scopolamine (1 mg/kg)–4 animals After 30 minutes of intraperitoneal second administration (saline or scopolamine), the animals were challenged to localize an underwater platform in a round recipient containing opaque water (water maze) and the escape latency (in seconds) was computed. If the animal did not locate the platform in 150 seconds, it was put in the platform for a 20 seconds period and then removed from the water. Tests were conducted twice a day, during 4 consecutive days.

As one could observe in FIGS. 1-4, animals from the control group reduce significantly of the escape latency in the third and fourth days of the test. When treated with scopolamine 30 minutes before the challenge, the animals could not learn the task and the escape latency approaches maximum values (150 s) in the fourth day of the test. Results from the injection of the compositions are shown in FIGS. 1-4.

The anticholinesterasic agent tacrine antagonize the induced amnesia by scopolamine, a significant effect in the fourth day of the study. The semi-synthetic alkaloid LASSBio-767 had a superior effect in relation to tacrine in the reversion of the induced amnesia by scopolamine, since the effect can be noticed in the second day of the treatment and is highly significant in the third and fourth days when the animals, although had received scopolamine (1 mg/kg), behave as the control group. The effect of the LASSBio-767 composition was also observed at 10 mg/kg concentrations. However, the LASSBio-822 alkaloid was not capable of antagonize the amnesia induced by scopolamine in rats in the water maze test.

c) Evaluation of the Amnesia Induced by Scopolamine in the Inhibitory Avoidance Assay A total of 120 adult male (25-30 g) Swiss mice were used. The animals were submitted to the inhibitory avoidance assay, which consists of a box with a base made of a grid connected to an electrostimulator (0.6 mA/3 s), and containing a wood platform (3 cm$^3$). Mice were put over this platform; being computed the latency (in seconds) until the animals put the four paws over the grid. In the first day of the test ("training"), animals would receive an adverse electrical stimulus (0.6 mA/3 s) whenever they stepped down to the grid (step down latency—SDL). At this stage, animals that would stay more than 15 seconds over the platform were discarded. Twenty-four hours later, the animals were re-introduced over the platform and the SDL computed ("retention").

Mice were divided into six experimental groups:

control=saline+saline saline+scopolamine (1 mg/kg)

LASSBio-767 (1 mg/kg)+scopolamine (1 mg/kg)

LASSBio-767 (10 mg/kg)+scopolamine (1 mg/kg)–4 animals

LASSBio-822 (1 mg/kg)+scopolamine (1 mg/kg)–4 animals

LASSBio-822 (3 mg/kg)+scopolamine (1 mg/kg)–4 animals

Figure 5:
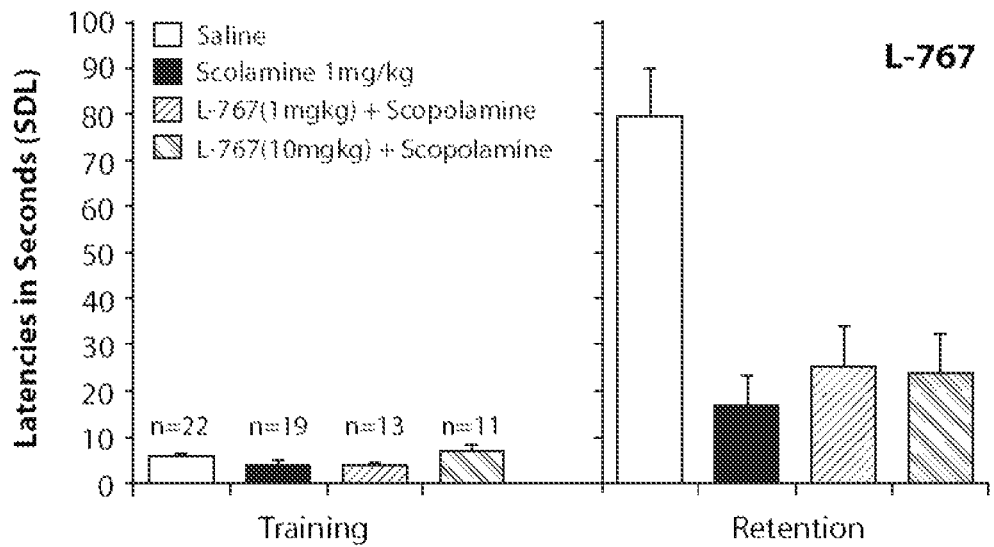
FIG. 5 presents the absence of the semi-synthetic alkaloid LASSBio-767, in the 1 and 10 mg/kg concentrations, in the reversion of amnesia induced by scopolamine in mice in the inhibitory avoidance assay. Latencies shown are from first (training) and second (retention) test days. Note that the animals treated with LASSBio-767 do not differ from the ones treated only with scopolamine. Values expressed as average and average standard deviation.
Figure 6:
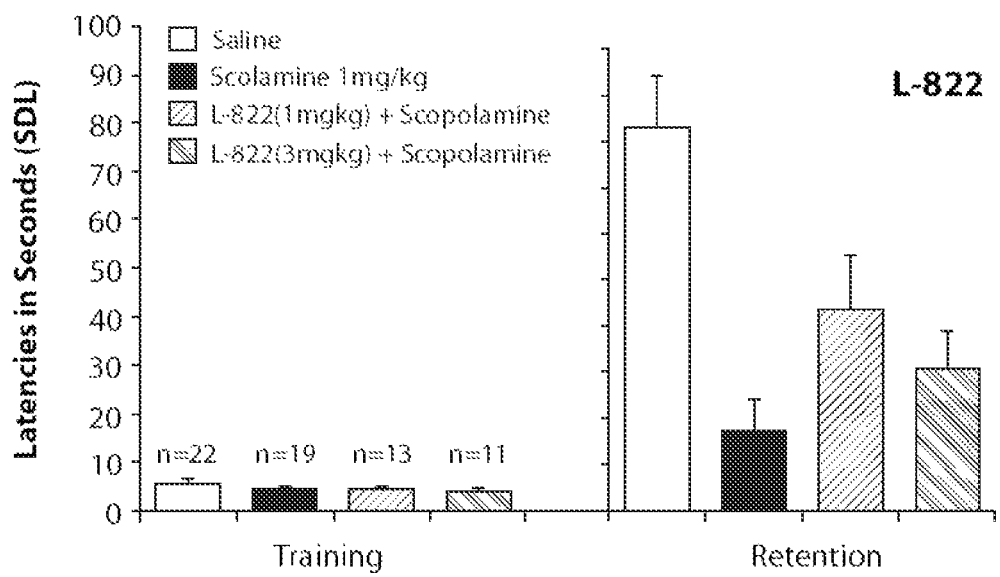
FIG. 6 presents the effect of alkaloid LASSBio-822, in the 1 and 3 mg/kg concentrations, in the reversion of amnesia induced by scopolamine in mice in the inhibitory avoidance assay. Latencies shown are from first (training) and second (retention) test days. Note that the animals previously treated with LASSBio-822 show a significant partial reversion of the amnesia induced by scopolamine. Values expressed as average and average standard deviation; $*p<0.05$; $**p<0.01$ Mann-Whitney test.
Figure 7:
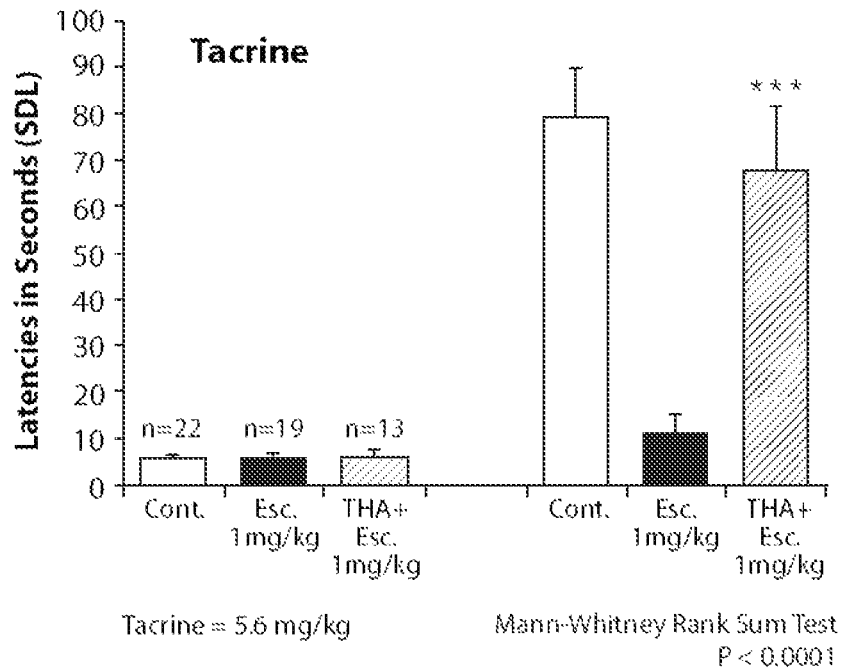
FIG. 7 presents the effect of tacrine, in the 5.6 mg/kg concentration, in the reversion of induced amnesia in the inhibitory avoidance assay. Latencies shown are from first (training) and second (retention) test days. Note that the animals previously treated with tacrine show a complete reversion of the amnesia induced by scopolamine. Values expressed as average and average standard deviation; $***p<0.001$ Mann-Whitney test.

It was observed that the alkaloid LASSBio-767, in both concentrations, did not present any effect on the amnesia induced by scopolamine. However, in this assay, the semi-synthetic alkaloid LASSBio-822 was capable of a significant reversion of the amnesia induced by scopolamine. In this assay, tacrine has totally reversed the effect of scopolamine. Results from this assay can be seen in FIGS. 5-7.

d) Evaluation of Cholinergic Side Effects Induced by Tacrine and LASSBio-767

Past 10 and 30 minutes after the I.P. administration of the drugs, the animals (n=10 mice/group) were observed in respect to the psicomotor activity in the open field test, lateral projection of rear paws, shivering, salivation, lachrymation, diarrhea, urination, and hypothermia. It was also verified the tacrine concentration capable of leading 50% of the animals to obit (LD50).

After the administration of tacrine (10 mg/kg), diarrhea and urination were observed in 70% of the mice. Moreover, this concentration of tacrine resulted in hypothermia and diminished motor activity. After administration of tacrine in concentrations superior to 30 mg/kg, all checked parameters are altered.

Figure 8:
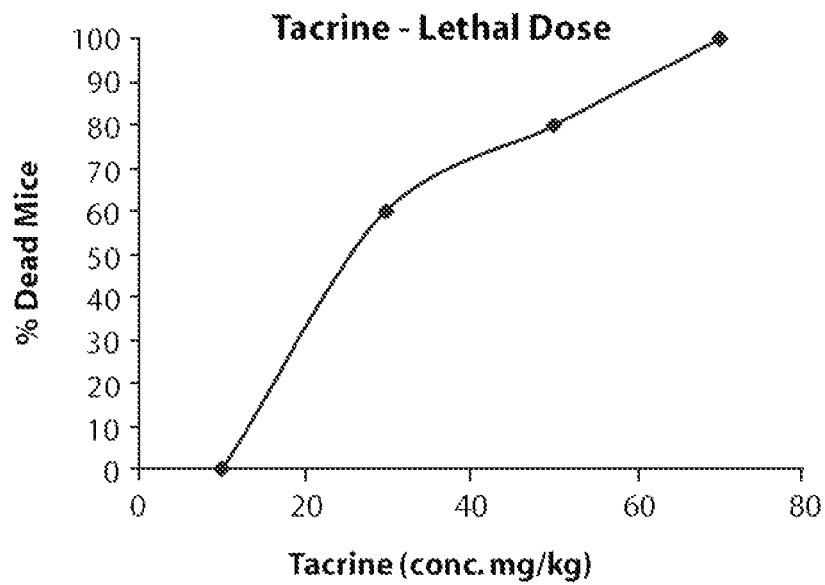
FIG. 8 presents the LD50 study of tacrine. The histogram shows the percentage of dead mice 10 to 30 minutes after the administration of different concentrations of tacrine.
Figure 9:
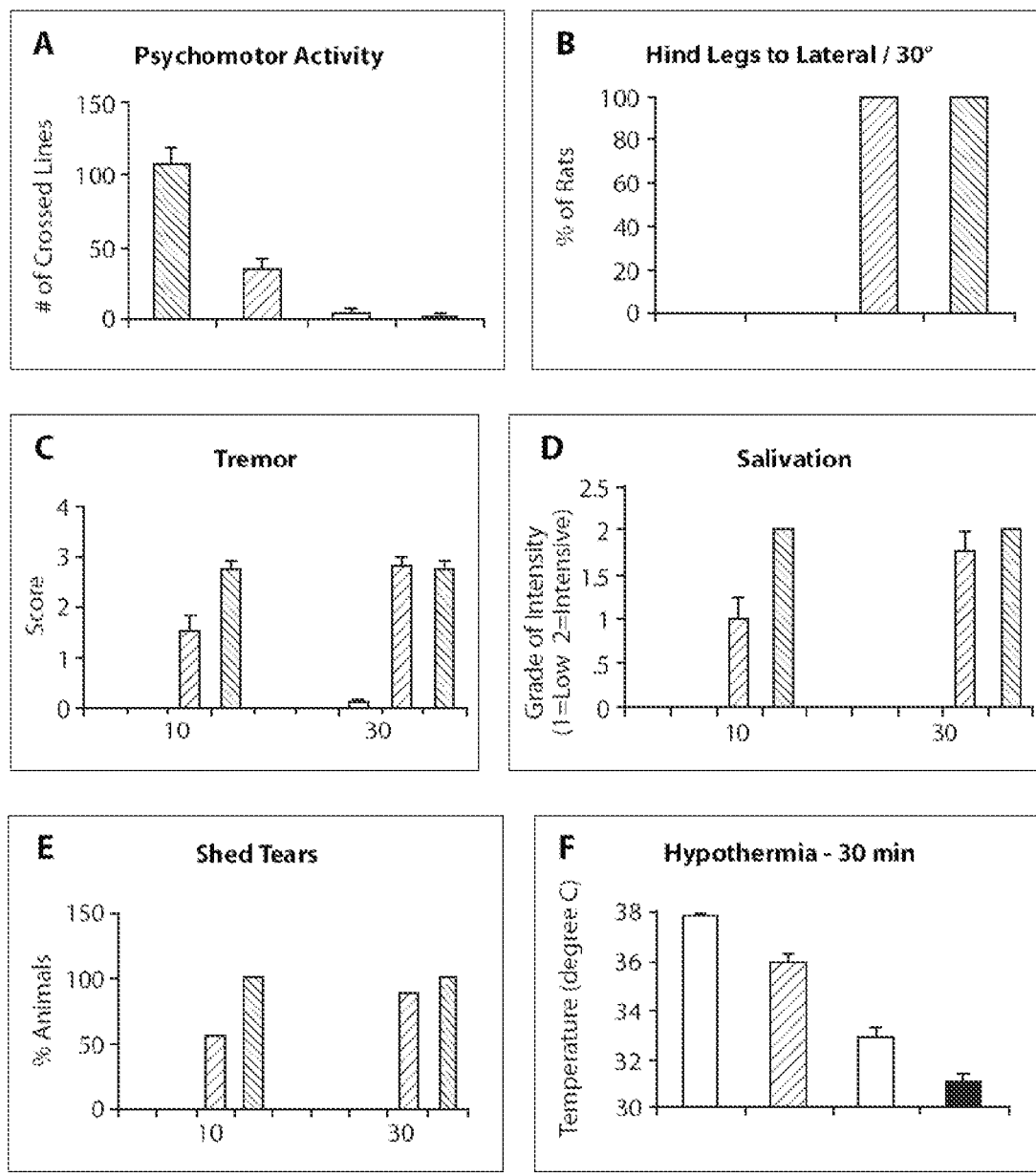
FIG. 9 presents the cholinergic side effects induced by the administration of saline (□), LASSBio-767 (▨), tacrine 10 mg/kg (▦), tacrine 30 mg/kg (▩), and tacrine 50 mg/kg (■), after 10 to 30 minutes of administration. Values expressed as average and average standard deviation.

Apart from mice, rats were observed after 30 minutes from administration of tacrine at 1 mg/kg (n=4), LASSBio-767 (n=12) and saline (n=12) and saline (n=12). Only animals treated with tacrine presented diarrhea after 30 minutes from administration and this symptom was observed in 100% of the animals. Results from this assay can be seen in FIGS. 8-9.

LASSBio-767 and LASSBio-822, at lower concentrations when compared to tacrine, were capable of reversing the amnesia induced by scopolamine in different models of learning and memory. On the other hand, no cholinergic side effects and no interference in the motor activity were observed with LASSBio-767 (10 mg/kg), which was observed with tacrine. In our studies, the therapeutic window of tacrine has proved to be too narrow. These results suggest a promising role of the studied compounds in the Alzheimer Disease therapeutics and in other pathologies associated to memory deficiency conditions. These compounds seem to have a superior efficacy and safety in comparison to drugs in clinically used today.

What is claimed is:

1. A process for the preparation of piperidinic derivatives of general formula (II)

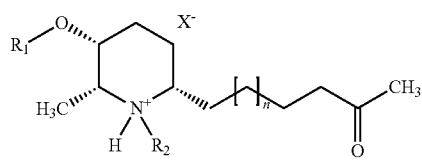

wherein:

n is 9;

$R_1$ is t-butoxycarbonyl;

$R_2$ is hydrogen, and

X is chloride;

or a pharmaceutically acceptable salt thereof;

comprising the step of submitting a piperidinic derivative of general formula (I)

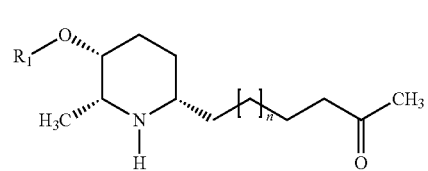

extracted alcoholic and/or hydroalcoholic from flowers and/or buds of plants of *C. spectabilis* to a reaction of acidification with strong acids.

2. The process according to claim 1, wherein the strong acid is hydrochloric acid.

3. A process for the preparation of piperidinic derivatives of general formula (III)

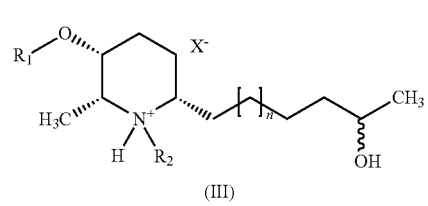

wherein:

n is 9;

$R_1$ is t-butoxycarbonyl;

$R_2$ is hydrogen, and

X is chloride;

or a pharmaceutically acceptable salt thereof;

comprising the step of submitting to a reduction reaction piperidinic derivatives of general formula (II)

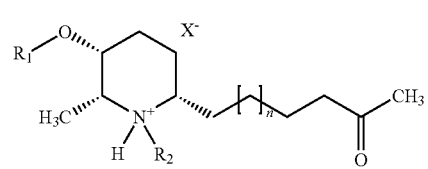

wherein:

n is 9;

$R_1$ is t-butoxycarbonyl;

$R_2$ is hydrogen, and

X is chloride;

or a pharmaceutically acceptable salt thereof;

that is prepared by a process comprising the step of submitting a piperidinic derivative of general formula (I)

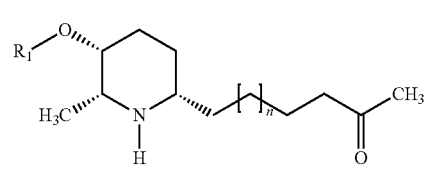

extracted alcoholic and/or hydroalcoholic from flowers and/or buds of plants of *C. spectabilis* to a reaction of acidification with strong acids.

4. The process according to claim 3, wherein the strong acid is hydrochloric acid.

\* \* \* \* \*